US008636719B2

(12) United States Patent
Wentling et al.

(10) Patent No.: US 8,636,719 B2
(45) Date of Patent: Jan. 28, 2014

(54) LUER CONNECTOR ASSEMBLY WITH CLAMPING SLEEVE AND METHOD OF USE

(75) Inventors: Angela Wentling, Sassamansville, PA (US); Timothy Schweikert, Levittown, PA (US)

(73) Assignee: Medical Components, Inc., Harleysville, PA (US)

( * ) Notice: Subject to any disclaimer, the term of this patent is extended or adjusted under 35 U.S.C. 154(b) by 1027 days.

(21) Appl. No.: 11/725,286

(22) Filed: Mar. 19, 2007

(65) Prior Publication Data

US 2007/0225684 A1 Sep. 27, 2007

Related U.S. Application Data

(60) Provisional application No. 60/785,613, filed on Mar. 24, 2006.

(51) Int. Cl.
*A61M 25/16* (2006.01)

(52) U.S. Cl.
USPC ............................ 604/534; 604/533; 604/538

(58) Field of Classification Search
USPC ............. 604/523, 533, 534, 167.01, 538, 250
See application file for complete search history.

(56) References Cited

U.S. PATENT DOCUMENTS

| 4,405,163 | A | 9/1983 | Voges et al. |
|---|---|---|---|
| 4,673,161 | A | 6/1987 | Flynn et al. |
| 5,035,399 | A | 7/1991 | Rantanen-Lee |
| 5,360,407 | A | 11/1994 | Leonard |
| 5,399,168 | A | 3/1995 | Wadsworth, Jr. et al. |
| 5,624,413 | A | 4/1997 | Markel et al. |
| 5,637,102 | A | 6/1997 | Tolkoff et al. |
| 5,833,654 | A | 11/1998 | Powers et al. |
| 6,113,572 | A | 9/2000 | Gailey et al. |
| 6,260,890 | B1* | 7/2001 | Mason ........................ 285/332 |
| 6,971,390 | B1 | 12/2005 | Vasek et al. |
| D544,600 | S | 6/2007 | Wentling |
| 7,344,527 | B2* | 3/2008 | Schweikert et al. .......... 604/533 |
| 2004/0064086 | A1* | 4/2004 | Gottlieb et al. ................. 604/43 |

(Continued)

FOREIGN PATENT DOCUMENTS

| DE | 3314640 | A1 | 4/1983 |
|---|---|---|---|
| DE | 3314640 | A1 * | 11/1983 .............. A61M 1/03 |

OTHER PUBLICATIONS

International Search Report and Written Opinion, PCT/US07/06812, dated Feb. 28, 2008 (7 pages).

(Continued)

*Primary Examiner* — Emily Schmidt
(74) *Attorney, Agent, or Firm* — Fox Rothschild LLP

(57) ABSTRACT

A luer connector assembly (100) including a luer connector body (102), a luer cap (110) and a protective flexible sleeve (120). The protective sleeve is assembled to the distal end (116) of the luer cap (110) to define a cap/sleeve subassembly (130), and the luer cap proximal end (112) is removably affixable to the distal end (106) of the luer connector (102). A prepared end (202) of a proximal catheter lumen (200) of a patient-implanted catheter assembly is inserted through the protective sleeve (120) and through and beyond the luer cap (110) to be affixed to the luer connector distal end (106). The luer cap/sleeve subassembly (130) is then slid proximally to be removably affixed to the luer connector distal end (106), whereafter the clamp (204) on the catheter lumen (200) is positionable onto and around the protective sleeve (120), to protect the catheter lumen (200) during clamping.

8 Claims, 2 Drawing Sheets

(56) References Cited

U.S. PATENT DOCUMENTS

2004/0249349 A1    12/2004   Wentling
2005/0107770 A1     5/2005   Schweikert et al.
2005/0124970 A1     6/2005   Kunin et al.
2007/0167931 A1*   7/2007   Waller et al. .................. 604/533

OTHER PUBLICATIONS

International Preliminary Report on Patentability dated Feb. 9, 2009; PCT/US2007/06812 (12 pages).

* cited by examiner

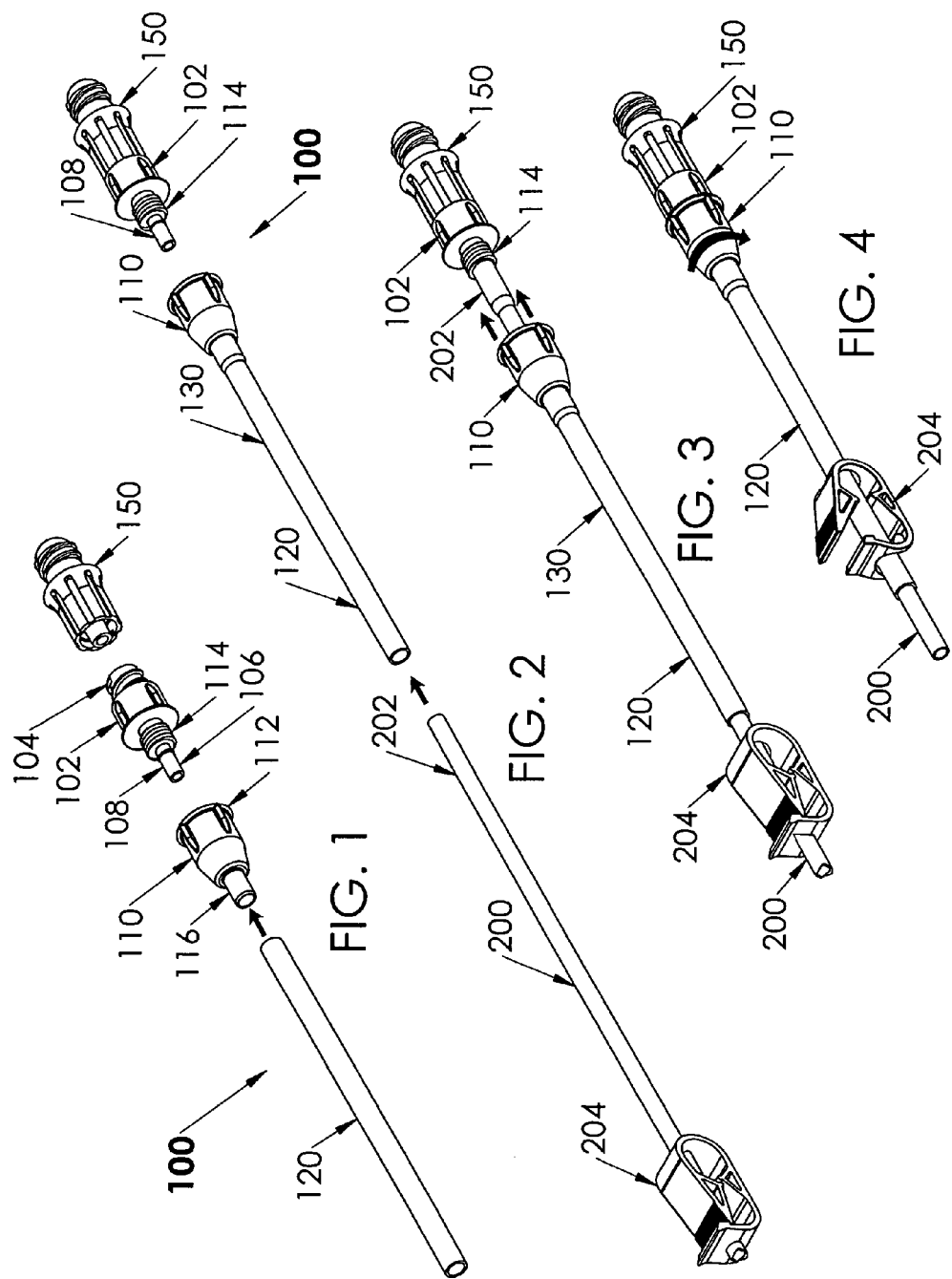

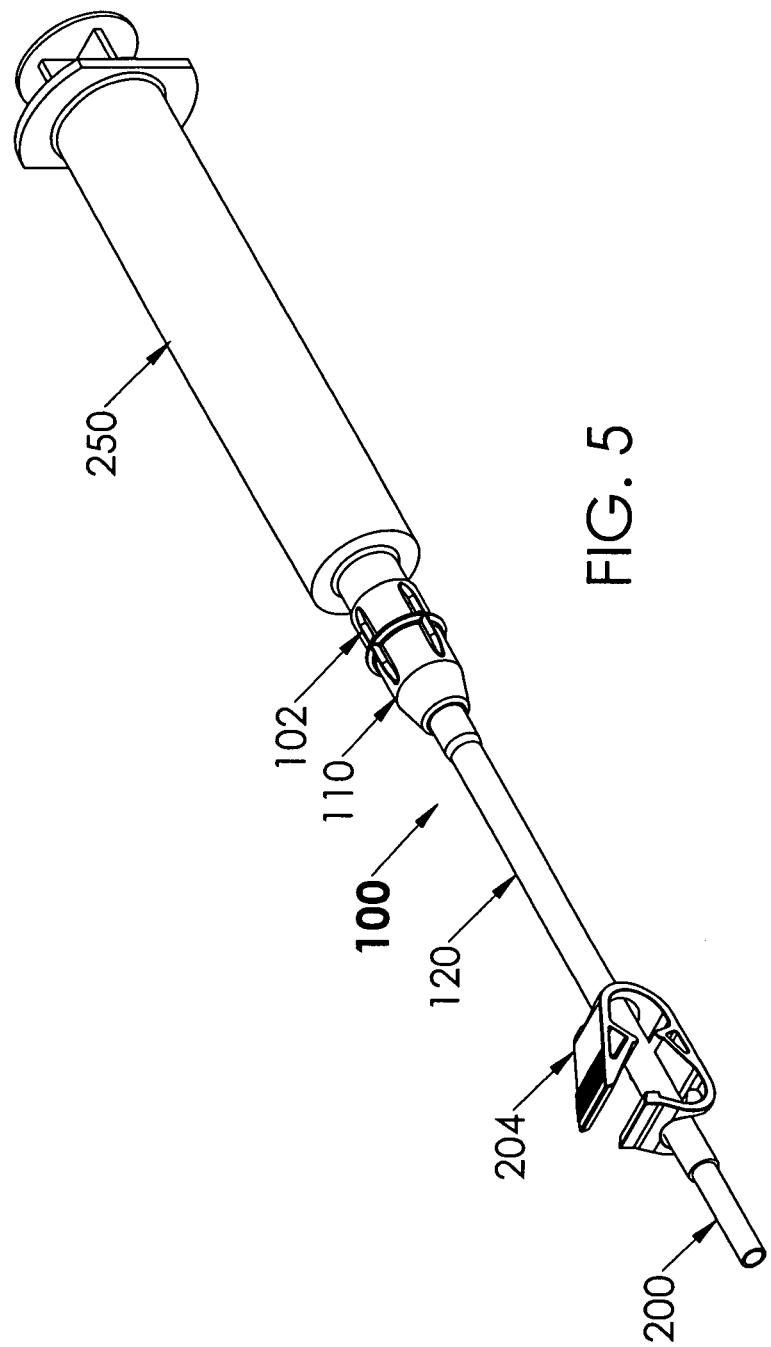

LUER CONNECTOR ASSEMBLY WITH CLAMPING SLEEVE AND METHOD OF USE

CROSS-REFERENCE TO RELATED APPLICATIONS

This application claims priority from U.S. Provisional Patent Application Ser. No. 60/785,613 filed Mar. 24, 2006.

FIELD OF THE INVENTION

The present invention relates to the field of medical devices and more particularly to catheters and catheter assemblies.

BACKGROUND OF THE INVENTION

Catheters may be located in various venous locations and cavities throughout the body of a patient for introduction of fluids to a body or removal of fluids from the body. Such catheterization may be performed by using a single catheter having multiple lumens. A typical example of a multiple lumen catheter is a dual lumen catheter assembly in which one lumen introduces fluid and the other lumen removes fluid. Catheterization may also be performed by using multiple single-lumen catheters, such as TESIO® catheters sold by Medical Components, Inc. of Harleysville, Pa.

A proximal end of each catheter lumen is typically connected to a distal end of an extension tube via a hub permanently secured to the catheter and the distal ends of the extension tubes. Each extension tube has a standard connector at its proximal end for connection to a medical device, such as a hemodialysis machine. Such connectors are commonly referred to as "luers". A luer includes standard male threads for connection of a proximal cap to the luer when the luer is disengaged from the hemodialysis machine to prevent blood from flowing out of the catheter. As a backup to the cap, a clamp, such as a Roberts clamp, is typically disposed over the extension tube. The clamp restricts fluid flow through the extension tube by compressing and closing the extension tube between a pair of clamp jaws. For long term catheterization, the clamp must be opened and closed numerous times, which may lead to a failure of the extension tube and blood loss from the catheter. It would be beneficial to provide an alternate method of providing a backup for the cap to secure the catheter between dialysis treatments.

The luer connector comprises a body having a proximal end, a distal end, and a passage extending therethrough between the proximal end and the distal end. The passage fluidly connects the proximal end and the distal end. The proximal end includes a fitting (or proximal cap) for releasably connecting the connector to an external device. The distal end is fluidly connected to a conduit, and a distal cap is commonly securable to the distal end of the luer connector to protect the connection of the luer connector to the conduit, which may be an extension tube or it may be a catheter lumen directly.

It has been observed that, after the catheter assembly has been placed in a patient, the catheter or extension tube on which the clamp is positioned may become damaged through several, or even one, cycles of clamping and unclamping. During repair of a patient-implanted catheter assembly, the luer connector is removed or severed from the extension tube, leaving a remaining length of extension tube extending from the hub and containing the clamp thereon, in the clamped state. Although repair kits may include a length of tubing for placement over the extension tube (or catheter) after the original luer connector is removed or severed from the extension tube (or catheter lumen), for being positioned within the clamp in order to protect the catheter lumen or extension tube, it is also often not utilized although expressly recommended.

It is desired to provide an efficacious way to assure that a physician can easily position the clamp on a protective sleeve over the catheter or extension tube following placement of a luer connector on the proximal end of a catheter lumen or its extension tube during repair.

BRIEF SUMMARY OF THE INVENTION

The present invention is a luer connector assembly for placement onto a proximal end of an extension tube (or directly onto a catheter lumen) of a patient-implanted catheter assembly during repair thereof, where the repair had resulted in removal, such as by severing, of the original luer connector on the proximal end of the extension tube of the catheter assembly, but where the original clamp is retained on the remaining proximal end of the extension tube (although a new clamp could be used to replace the original clamp). The connector includes the luer connector body, a distal luer cap and a length of flexible protective sleeve. The luer connector body includes a standard threaded proximal end and a distal end that includes a connection section for being affixed to the proximal end of the extension tube; the distal luer cap is removably affixable onto the luer connector distal end after connection with the extension tube; the protective sleeve is assembled directly to the cap and extending distally therefrom for a selected length to define a cap/sleeve subassembly.

The present invention also comprises a method of use. During assembly of the luer connector and luer cap/sleeve subassembly to the extension tube, the luer cap/sleeve subassembly is placed onto the newly defined proximal end of the extension tube until the proximal tube end is exposed to be affixed to the luer connector distal end. The subassembly is then slid proximally to the distal end of the luer connector (affixed to the extension tube) and the cap is then affixed to the luer connector distal end. The clamp originally on the extension tube is then positionable around the protective sleeve by being slid proximally from the extension tube where it was previously positioned.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings:

FIG. 1 is an isometric view of the present invention with the luer connector, a proximal cap, and a luer cap and protective sleeve exploded;

FIG. 2 is an isometric view of the protective sleeve secured onto the luer cap, and the luer cap/sleeve and luer connector positioned to be affixed to the proximal end of an extension tube (or catheter lumen), and showing a clamp on the extension tube in a clamping state;

FIG. 3 is an isometric view similar to FIG. 2, wherein the extension tube is affixed to the luer connector, showing the clamp still in a clamping state on the extension tube;

FIG. 4 is an isometric view illustrating the luer connector and luer cap/sleeve fully affixed to the proximal end of the extension tube, with the proximal cap on the luer connector proximal end and also showing the clamp slid onto the protective sleeve and in an unclamped state; and FIG. 5 is similar to FIG. 4 showing a syringe in position connected onto the proximal end of the luer connector assembly, rather than a proximal cap.

DETAILED DESCRIPTION OF THE INVENTION

Certain terminology is used herein for convenience only and is not to be taken as a limitation on the present invention. The terms "distal" and "proximal" refer, respectively, to directions closer to and farther away from, respectively, a patient insertion end of the catheter with which the present invention is to be used. The terminology includes the words specifically mentioned, derivatives thereof and words of similar import. The embodiments illustrated below are not intended to be exhaustive or to limit the invention to the precise form disclosed. These embodiments are chosen and described to best explain the principle of the invention and its application and practical use and to enable others skilled in the art to best utilize the invention.

The luer connector assembly 100 of the present invention includes the luer body 102 containing a threaded proximal end 104 and a distal end 106 that includes an axially extending flange 108 for inserting into the proximal end 202 (FIGS. 2 to 5) of the extension tube (or catheter lumen) 200 in a force fit, a cap 110 for threading onto the luer connector distal end 106, and a protective sleeve 120 affixed to the cap 110 and extending distally therefrom for a selected length. The luer cap 110 includes a proximal section 112 to be threaded onto the threaded portion 114 of the distal end 106 of the luer connector, and a distal flange section 116 extending distally therefrom. An end of the protective sleeve 120 is force fit onto the distal flange section 116 to define a cap/sleeve subassembly 130 that for convenience may be preassembled to the luer connector prior to being utilized in the repair of a extension tube 200. Also shown is a proximal luer cap 150 for being releasably connected onto the proximal end of the luer body 102 and that serves to close off and seal the passageway of the extension tube and catheter lumen when the luer connector assembly of the present invention is fully connected onto the proximal end of the extension tube.

A clamp 204, such as a Roberts clamp, is shown in FIGS. 2 to 5, that is also originally part of the patient-implanted catheter assembly (not shown), and used to clamp shut the extension tube during the period when the catheter assembly has been disconnected from a hemodialysis machine or other instrument or apparatus, for example. To close off and seal the extension tube, and thus the catheter lumen, during repair, clamp 204 is manipulated into its clamping state, closing the extension tube, and the original luer connector is severed from the proximal end of the extension tube (or catheter lumen); a portion of the extension tube remains that will be referred to hereinafter as the prepared proximal end.

During assembly of the luer connector body 102 and cap 110 to the prepared proximal end 202 of the extension tube 200, the proximal cap 150 is connected onto the proximal end of luer connector body 102, and the luer cap/sleeve subassembly 130 is unthreaded from the distal end of the luer connector 102. Then, the luer cap/sleeve subassembly 130 is placed onto and over the remaining proximal end 202 of the extension tube 200. The proximal end of the extension tube 200 is then slid to the distal end of the luer connector 110 in a force fit over the distal flange. The luer cap/sleeve subassembly 130 is now connected onto the distal end of the luer connector body 102, which has been affixed to the extension tube 200. The clamp 204 originally on the extension tube is now unclamped and then slid proximally to become positioned over and around the protective sleeve 120. Thereafter, the repaired extension tube is protected during subsequent clamping by the protective sleeve.

FIG. 5 illustrates using a syringe 250 releasably connected to the proximal end of luer connector 100, instead of the proximal luer cap 150. Syringe 250 serves to close off and seal the passageway of the extension tube and catheter lumen so that clamp 204 may be unclamped for being moved proximally onto the protective sleeve.

The present invention thus provides a protective sleeve that is easily used by the physician during catheter assembly repair, instead of a loose piece protective sleeve.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A luer connector assembly for use in repairing a proximal end of a catheter assembly having its distal end implanted in a patient, the catheter assembly proximal end portion having been prepared for repair and including a clamp disposed therealong for closing and opening a catheter lumen, comprising:

a protective sleeve component having a luer cap affixed to a proximal end length of flexible compressible tubing, the flexible compressible tubing being slidable over and along a prepared catheter assembly proximal end portion, the length of flexible compressible tubing being sufficiently elongated for a clamp to be disposed thereover and therealong, and an initially separate luer connector for facilitating coupling of the catheter assembly to a corresponding medical device when affixed to the prepared proximal end of the catheter assembly by the practitioner, wherein the luer cap has a proximal end configured to be coupled to a complementary distal end of the luer connector by a practitioner during catheter repair, wherein a proximal end length of a catheter lumen having a clamp thereon spaced from the proximal end of the catheter lumen, is insertable through the protective sleeve component for the proximal end of the catheter lumen to protrude beyond a proximal sleeve end to be affixed to the distal end of the luer connector, whereafter the protective sleeve component is slidable as a unit for the luer cap to engage and be coupled to the luer connector and thus cover the connection of the catheter lumen proximal end to the luer connector, whereafter the clamp disposed initially on the proximal catheter end is slidable onto and over the protective sleeve component to protect the catheter lumen during subsequent clamping thereof.

2. The luer connector assembly of claim 1, wherein the protective sleeve component is force fit over a distally extending flange of the luer cap.

3. The luer connector assembly of claim 1, wherein the luer cap is removably threadedly engageable with a portion of the distal end of the luer connector.

4. The luer connector assembly of claim 1, wherein the distal end of the luer connector includes a distally extending flange insertable into a end opening of the proximal end of the catheter to be affixed thereto.

5. A method of assembling a luer connector assembly to a proximal end of a catheter lumen of a catheter assembly having its distal end implanted in a patient, for repair of the proximal end thereof by a practitioner, comprising the steps of:

preparing a proximal end of a catheter lumen of an implanted catheter assembly having a clamp disposed therealong proximate the proximal end for closing and opening the catheter lumen;

providing a luer connector assembly including a luer connector and a protective sleeve component having a luer cap affixed to a length of flexible compressible tubing, the protective sleeve component being initially separate from the luer connector, and the protective sleeve component being slidable over and along the prepared catheter proximal end and is sufficiently elongated for a clamp to be disposed therealong;

positioning the protective sleeve component onto the proximal end section of the catheter lumen such that the luer cap is near to but spaced from the proximal end of the catheter lumen, such that the proximal end of the catheter lumen protrudes proximally beyond the luer cap;

affixing the protruding proximal end of the catheter lumen to a distal end of the luer connector;

sliding the protective sleeve component in the proximal direction over the catheter proximal end section and affixing the luer cap to the distal end of the luer connector over the connection of the luer connector and catheter lumen; and unclamping and sliding the clamp from the catheter lumen over and onto the elongated protective sleeve to protect the catheter lumen during subsequent clamping thereof.

6. The method as set forth in claim 5, wherein the length of flexible compressible tubing is force fitted onto and over a distally extending flange of the luer cap distal end.

7. The method as set forth in claim 5, wherein a luer cap proximal end is threadably engageable with the distal end of the luer connector.

8. The method as set forth in claim 5, wherein the affixing of the catheter lumen proximal end to the luer connector includes the step of force fitting a distally extending flange of the distal end of the luer connector into and within the catheter lumen proximal end.

* * * * *